US00PP24734P2

(12) United States Plant Patent
Jones et al.

(10) Patent No.: US PP24,734 P2
(45) Date of Patent: Aug. 5, 2014

(54) ***ALONSOA* PLANT NAMED 'PENSCAR'**

(50) Latin Name: *Alonsoa×meridionalis*
Varietal Denomination: PENSCAR

(71) Applicant: Planthaven International, Inc, Santa Barbara, CA (US)

(72) Inventors: Sidney James Jones, Gwent (GB); David James Jones, Caldicot (GB)

( * ) Notice: Subject to any disclaimer, the term of this patent is extended or adjusted under 35 U.S.C. 154(b) by 91 days.

(21) Appl. No.: 13/694,634

(22) Filed: Dec. 20, 2012

Related U.S. Application Data

(60) Provisional application No. 61/632,098, filed on Jan. 17, 2012.

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Barbara Campbell; Cochran Freund & Young LLC

(57) ABSTRACT

A new and distinct cultivar of *Alonsoa* plant named 'PENSCAR' that is characterized by a compact and upright habit, green and white-cream variegated leaves, and bright scarlet single flowers. In combination these traits set 'PENSCAR' apart from all other existing varieties of *Alonsoa* known to the inventor.

2 Drawing Sheets

Genus: *Alonsoa.*
Species: ×*meridionalis.*
Denomination: 'PENSCAR'.

BACKGROUND OF THE INVENTION

The present invention relates to a new and distinct cultivar of *Alonsoa*, which is grown as an ornamental tender perennial plant for use in the garden and landscape. The new cultivar is known botanically as *Alonsoa×meridionalis*, and will be referred to hereinafter by the cultivar name 'PENSCAR'. 'PENSCAR' was discovered by the inventors in 2007 as a naturally occurring variegated branch sport. The branch sport was observed on a single plant in a seed-raised crop of *Alonsoa×meridionalis* (species, unpatented) growing in the inventors' nursery in Caldicot, Monmouthshire, United Kingdom.

'PENSCAR' exhibits a compact upright habit, prominently variegated and serrated leaves and bright scarlet flowers. 'PENSCAR' grows to 70 cm. in height and 40 cm. in width during a one year growing season. 'PENSCAR' exhibits its distinguishing characteristics to best effect when grown in full sun or light shade, with moderate water. There are no particular pests or diseases known to the inventor which affect 'PENSCAR'. 'PENSCAR' is hardy to at least in USDA Zone 9.

The closest comparison plant known to the inventor is the non-variegated parent variety, a seed-raised plant of the species *Alonsoa×meridionalis*. 'PENSCAR' is distinguishable from the comparison plant by its variegated leaves. In other respects, including the bright scarlet flowers, 'PENSCAR' is indistinguishable from its parent.

'PENSCAR' was first asexually propagated by the inventors in April 2007 in Caldicot, Monmouthshire, United Kingdom. Asexual propagation was accomplished using tip cuttings. Since that time, under careful observation, the distinguishing characteristics of 'PENSCAR' have been determined stable and uniform, and to reproduce true to type in successive generations of asexual propagation.

The inventors filed an application for European Community Plant Breeders' Rights for 'PENSCAR' on Oct. 29, 2010, Serial Number 2010/2161. At the time of filing the application for European Community Plant Breeders' Right cited above, and until February 2011, all plants of 'PENSCAR' remained at the inventors' nursery under the inventors' control. The first public distribution of any plants of 'PENSCAR' took place in February 2011 when the inventors commenced deliveries of plants to wholesale growers in the United Kingdom.

SUMMARY OF THE INVENTION

The distinguishing characteristics of 'PENSCAR' are as follows: In combination these traits set 'PENSCAR' apart from all other existing varieties of *Alonsoa* known to the inventors. 'PENSCAR' has not been tested under all possible conditions and phenotypic differences may be observed with variations in environmental, climatic, and cultural conditions.

1. Plants of 'PENSCAR' exhibit a compact and upright growth habit.
2. The leaves of 'PENSCAR' are variegated.
3. The leaves of 'PENSCAR' are predominantly mid-green in color, with contrasting white to cream margins.
4. 'PENSCAR' bears bright scarlet single flowers.
5. After one year of unrestricted growth, plants of 'PENSCAR' are 70 cm in height and 40 cm in width.
6. 'PENSCAR' prefers full sun in rich well-drained soil.
7. 'PENSCAR' is a tender perennial which survives in USDA Zone 9 or warmer.

BRIEF DESCRIPTION OF THE DRAWINGS

The accompanying color drawings illustrate the overall appearance of 'PENSCAR' showing the colors of its foliage and flowers as true as it is reasonably possible to obtain in colored reproductions of this type.

The drawings were made from one year old plants of 'PENSCAR' which were photographed in the fall at the inventors' nursery in Caldicot, Monmouthshire, United Kingdom.

The drawing labeled

The drawing labeled

BOTANICAL DESCRIPTION OF THE PLANT

Figure 1:
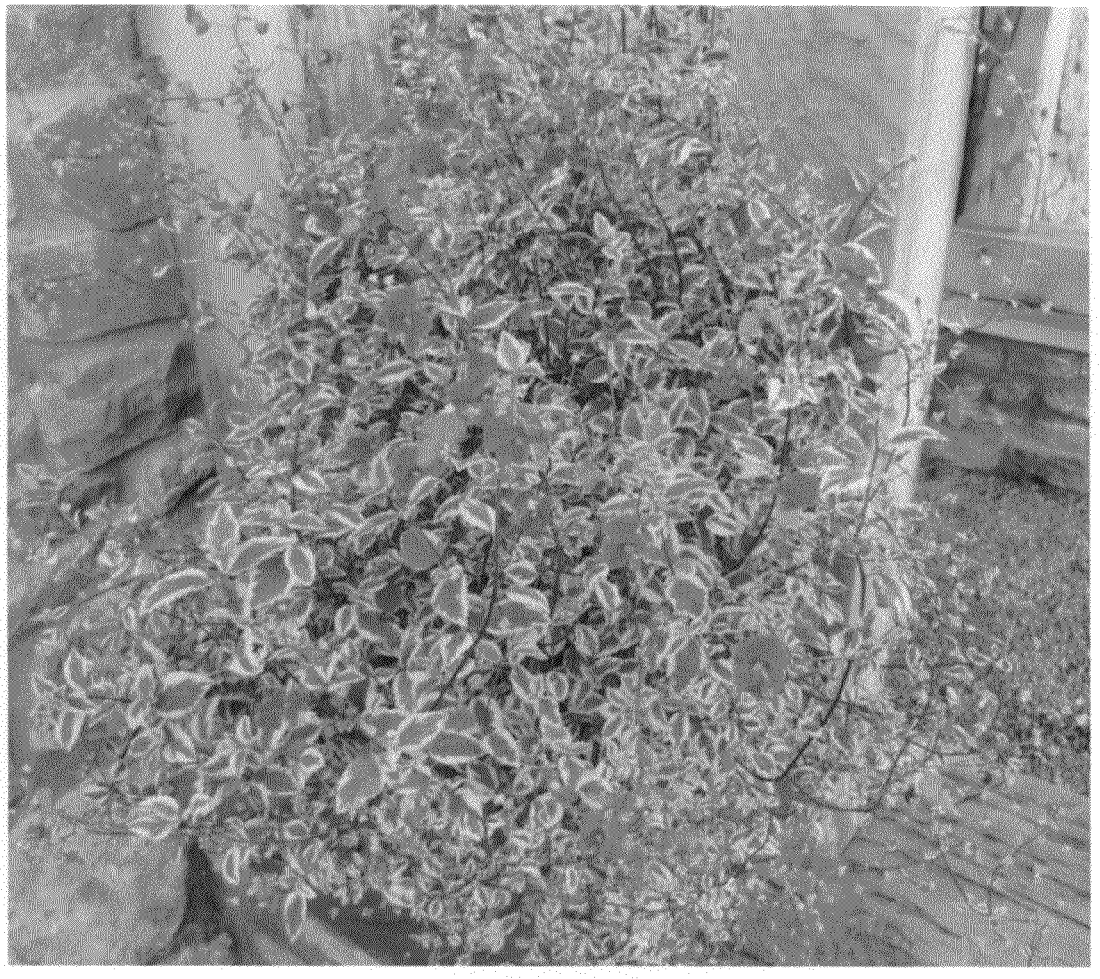
FIG. 1 depicts an entire flowering plant of 'PENSCAR'.
Figure 2:
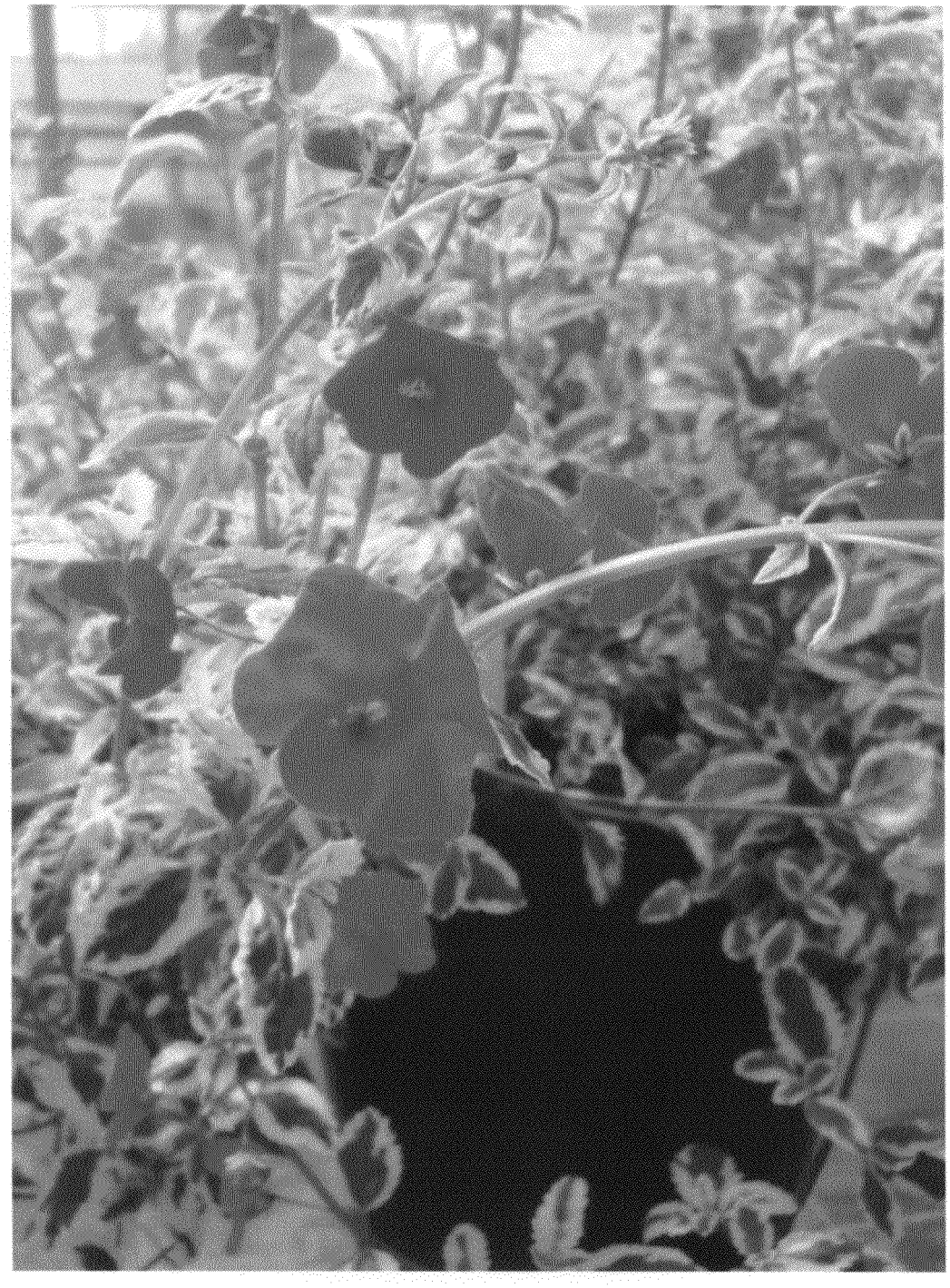
FIG. 2 depicts a close-up view of the flowers of 'PENSCAR'.

The following is a detailed botanical description of the new *Alonsoa* cultivar named 'PENSCAR'. Observations, measurements, values and comparisons were collected from a plant grown out-of-doors in Santa Barbara, Calif. The observed plant was approximately nine months old and was growing in a 1 gallon container. The plant had been grown without the use of growth retardant chemicals or any pinching. Color determinations were made in accordance with The 2001 Royal Horticultural Society Colour Chart from London, England, except where general color terms of ordinary dictionary significance are used. The growing requirements of the new variety 'PENSCAR' are similar to the species.

Botanical classification: *Alonsoa×meridionalis* 'PENSCAR'.
Family: Scrophulariaceae.
Genus: *Alonsoa*.
Species: *×meridionalis*.
Denomination: 'PENSCAR'.
Common name: None known.
Habit and shape: Compact and upright.
Commercial category: Tender perennial.
Use: As a bedding plant or container plant or for mixed combination plantings.
Suggested commercial container size: 9 cm container and larger.
Parentage: The new variety *Alonsoa×meridionalis* 'PENSCAR' was discovered as a variegated branch sport on a seed-raised plant of the species *Alonsoa×meridionalis*.
Propagation method: Vegetative cuttings.
Rooting system: Fine.
Vigor: Slow to establish, moderately vigorous once established.
Crop time (average): 6 months to produce a flowering plant in 9 cm container from an unrooted cutting.
Mature height (average): 70 cm.
Mature width (average): 40 cm.
Cultural requirements: Performs best in full sun, with moderate water, and most soil types.
Pest and disease susceptibility: None known to the inventors.
Hardiness: Survives in USDA Zone 9 and warmer.
Special growing recommendations: Occasional pinching out of new growth will improve lateral branching and number of flowers.

Stems:
- *Branching habit*.—Both basal and lateral branching.
- *Basal stem quantity*.—Approximately 10 basal stems produced in one season.
- *Lateral stem quantity*.—Approximately 8-10 lateral stems per basal stem.
- *Stem shape*.—Cylindrical.
- *Surface*.—Glabrous.
- *Stem color*.—Juvenile 152D, mature 173A.
- *Stem length*.—40-60 cm.
- *Stem diameter*.—2-3 mm.
- *Stem strength*.—Moderately strong, wiry.
- *Internode* (*average*).—1.5 cm.

Foliage:
- *Leaf arrangement*.—Opposite, in pairs or in threes.
- *Leaf division*.—Simple.
- *Leaf margin*.—Coarsely and irregularly serrate.
- *Leaf surface* (*both surfaces*).—Glabrous.
- *Leaf shape*.—Ovate to lanceolate, moderately convex.
- *Leaf length*.—18-25 mm.
- *Leaf width* (*average*).—12-16 mm.
- *Leaf color* (*mature leaf, both surfaces*).—143A with white-cream margin ranging between NN155B and NN155D.
- *Leaf color* (*juvenile leaf, both surfaces*).—143A with yellow margin 13C.
- *Leaf apex*.—Acute.
- *Leaf base*.—Cuneate.
- *Venation pattern*.—Pinnate.
- *Vein color* (*both surfaces*).—As adjacent leaf tissue.
- *Attachment*.—Petiolate.
- *Petiole surface*.—Glabrous.
- *Petiole color*.—152B.
- *Petiole dimensions*.—8 mm in length and 1 mm in diameter.

Inflorescence:
- *Type*.—Solitary flower.
- *Arrangement*.—Axillary.
- *Flower dimensions* (*average*).—15 mm in length and 12 mm in width.
- *Blooming months*.—Sparsely in May and June, prolifically in August to October.
- *Flower quantity* (*average mid-summer*).—16 per lateral stem.
- *Flower aspect*.—Nodding and outward facing.
- *Flower type*.—Single.
- *Persistent or self-cleaning*.—Self-cleaning.
- *Peduncle shape*.—Cylindrical.
- *Peduncle surface*.—Glabrous.
- *Peduncle color*.—152B towards stem, 173A towards calyx.
- *Peduncle dimensions* (*average*).—20-25 mm in length and 1 mm in diameter.
- *Axillary peduncle angle*.—45°.
- *Bud shape*.—Obovate.
- *Bud apex*.—Rounded.
- *Bud color*.—Emerges 41D, soon becoming 41A.
- *Rate of opening*.—Rapid, from 1-2 days from visible bud to fully open flower.
- *Bud surface*.—Glabrous.
- *Bud dimensions*.—3 mm in depth and 2 mm in diameter.
- *Corolla shape*.—Campanulate, 5-lobed.
- *Corolla dimensions*.—Short tube, 2 mm in depth and 2 mm. in diameter.
- *Corolla surface* (*both surfaces*).—Glabrous.
- *Lobes* (*petals*).—5 in number.
- *Lobe arrangement*.—Rotate, each lobe rotundate, one lobe larger than other four lobes. Larger lobe uppermost.
- *Lobe dimensions* (*larger lobe*).—10 mm in height, 8 mm in width.
- *Lobe dimensions* (*four equal lobes*).—8 mm in height, 7 mm in width.
- *Lobes fused or unfused*.—Basally fused.
- *Lobe color* (*both surfaces*).—41A.
- *Lobe margin*.—Entire.
- *Lobe shape*.—Obovate.

*Lobe surface* (*both surfaces*).—Glabrous.
*Lobe apex*.—Obtuse.
*Calyx shape*.—Campanulate.
*Calyx color*.—143A with yellow margin 13C.
*Calyx dimensions*.—4 mm in depth, 3 mm in diameter.
*Sepals*.—5 in number.
*Sepal shape*.—Narrow elliptic.
*Sepal dimensions*.—4 mm in length and 1 mm in width.
*Sepals fused or unfused*.—Basally fused.
*Sepal color* (*both surfaces*).—143A with yellow margin 13C.
*Sepal margin*.—Entire.
*Sepal apex*.—Acute.
*Sepal surface* (*both surfaces*).—Glabrous.
*Flower fragrance*.—None observed.

Reproductive organs:
*Stamens*.—4 in number, length approximately 2 mm, color 10A.
*Anthers*.—Dorsifixed, oblong, 1 mm in length, 0.75 mm in width, color: 12B.
*Pollen amount*.—Minimal, color: 12B.
*Pistil*.—1 in number, length 7 mm, color: 164C.
*Stigma*.—Capitate, 2 mm in diameter, color 153A.
*Ovary position*.—Superior.
*Seeds*.—Plant is sterile.

The invention claimed is:

1. A new and distinct cultivar of *Alonsoa* plant named 'PENSCAR' as described and illustrated herein.

* * * * *